(12) United States Patent
Carlson et al.

(10) Patent No.: US 7,062,323 B2
(45) Date of Patent: Jun. 13, 2006

(54) MAXIMUM ATRIAL TRACKING RATE FOR CARDIAC RHYTHM MANAGEMENT SYSTEM

(75) Inventors: Gerrard M. Carlson, Champlin, MN (US); Julio C. Spinelli, Shoreview, MN (US); Qingsheng Zhu, Little Canada, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 628 days.

(21) Appl. No.: 10/040,287

(22) Filed: Oct. 19, 2001

(65) Prior Publication Data

US 2003/0078624 A1   Apr. 24, 2003

(51) Int. Cl.
 *A61N 1/18*   (2006.01)
(52) U.S. Cl. .............................. 607/9; 607/14; 600/528
(58) Field of Classification Search .................... 607/9, 607/14, 19, 25; 600/528
See application file for complete search history.

(56) References Cited

U.S. PATENT DOCUMENTS

| | | | |
|---|---|---|---|
| 4,624,260 A | 11/1986 | Baker, Jr. et al. | 128/419 PG |
| 5,156,147 A | 10/1992 | Warren et al. | 128/419 PG |
| 5,235,976 A | 8/1993 | Spinelli | 607/25 |
| 5,316,001 A | 5/1994 | Ferek-Petric et al. | 128/661.08 |
| 5,540,725 A | 7/1996 | Bornzin et al. | 607/9 |
| 5,609,613 A | 3/1997 | Woodson et al. | 607/19 |
| 5,792,195 A | 8/1998 | Carlson et al. | 607/17 |
| 6,119,040 A | 9/2000 | Chirife | 607/18 |
| 6,135,970 A | 10/2000 | Kadhiresan et al. | 600/595 |
| 6,151,524 A | 11/2000 | Krig et al. | 607/14 |
| 6,256,536 B1 | 7/2001 | Kramer | 607/9 |
| 6,263,243 B1 | 7/2001 | Lang | 607/17 |

FOREIGN PATENT DOCUMENTS

| | | |
|---|---|---|
| EP | 0526798 | 10/1993 |
| WO | WO-01/10499 | 2/2001 |

OTHER PUBLICATIONS

"Examination Report, Application No. 02 802 141.8-2304, date mailed Apr. 26, 2005", 4 Pages.
"International Search Report, Application No. PCT/US02/32891, date mailed Jan. 15, 2003", 5 Pages.

*Primary Examiner*—Mark Bockelman
(74) *Attorney, Agent, or Firm*—Schwegman, Lundberg, Woessner & Kluth, P.A.

(57) ABSTRACT

A cardiac rhythm management system includes an operational mode in which ventricular pacing pulses are delivered at a rate that tracks a sinoatrial rate up to an appropriate maximum atrial tracking rate (MATR) value determined by the system. In one example, the MATR value is based on a patient activity level and a hemodynamic maximum rate (HMR) determined from a QRS-to-$S_2$ interval, where $S_2$ is an accelerometer-generated fiducial correlative to aortic valve closure (AVC). In a further example, a correlation between the QRS-to-$S_2$ interval and heart rate is established, and the MATR is based on the patient activity level and heart rate. In a further example, a lower rate threshold for providing antitachyarrhythmia therapy is modified based on the MATR. For example, when the MATR exceeds a default value of the antitachyarrhythmia therapy lower rate threshold, the threshold tracks the MATR. In another example, the MATR is based on an active time between a QRS complex and a heart impedance signal maximum slope during the same cardiac cycle.

42 Claims, 3 Drawing Sheets

MAXIMUM ATRIAL TRACKING RATE FOR CARDIAC RHYTHM MANAGEMENT SYSTEM

TECHNICAL FIELD

This document relates generally to cardiac rhythm management systems and particularly, but not by way of limitation, to such a system including an operational mode in which pacing pulses are delivered at a rate that tracks a sinoatrial rate up to an appropriate maximum atrial tracking rate value determined by the system.

BACKGROUND

When functioning properly, the human heart maintains its own intrinsic rhythm based on physiologically-generated electrical impulses. It is capable of pumping adequate blood throughout the body's circulatory system. Each complete cycle of drawing blood into the heart and then expelling it is referred to as a cardiac cycle.

However, some people have irregular or other abnormal cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers coordinate atrial and ventricular contractions to improve pumping efficiency.

Cardiac rhythm management systems also include defibrillators that are capable of delivering higher energy electrical stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is determining the rate at which pacing pulses are delivered to the heart. Some systems include one or more operational modes referred to as atrial tracking modes. In an atrial tracking mode, the system detects atrial heart contractions triggered by the heart's "physiological pacemaker," referred to as the sinoatrial node. Based on the rate of the detected heart contractions, the system determines the rate of pacing pulses delivered to a ventricle. Such an atrial tracking mode is useful in a patient having a functional sinoatrial node, but where the patient has an atrioventricular node that fails to conduct physiological electrical impulses from the atrium to the ventricle. Some cardiac rhythm management systems further include one or more rateresponsive atrial tracking modes. In a rate-responsive atrial tracking mode, the system adjusts the rate of ventricular pacing pulses based not only on the rate of atrial heart contractions, but also based on a physiologic sensor-indication of the patient's metabolic need for increased blood circulation. One example of such a sensor is an accelerometer that detects the patient's activity for providing an indication of a need for a higher pacing rate. Another example is a ventilation/respiration sensor that detects the patient's breathing rate for providing an indication of a need for a higher pacing rate. In one implementation of a rateresponsive atrial tracking mode, the ventricular pacing rate is based on the detected atrial heart rate unless the physiologic sensor indicates a need for an even higher ventricular pacing rate.

In both the atrial tracking mode and the rate-responsive atrial tracking mode, the system typically includes a maximum atrial tracking rate (MATR). The MATR imposes a limit beyond which the ventricular rate does not track the detected atrial heart rate. The MATR limit prevents pacing the ventricle at a dangerously high rate during an atrial tachyarrhythmia. One example of a cardiac rhythm management device includes a MATR of 120 beats per minute (bpm) as a factory default value. The physician can adjust the MATR at the time that the cardiac rhythm management device is implanted in the patient. The present inventors have recognized that without additional clinical data informing the physician of an appropriate MATR value for a particular patient, the physician typically must settle for programming the MATR to an overly conservative value that may be inappropriately low for the particular patient, thereby limiting the patient's ability to exercise or engage in activity at higher heart rates. Moreover, cardiac rhythm management devices typically include a multitude of programmable parameters that can be adjusted by the physician at the time of implant, increasing the complexity and time required for the implant procedure. Accordingly, the present inventors have recognized that there is a need for a cardiac rhythm management system that automatically determines an appropriate MATR value.

SUMMARY

A cardiac rhythm management system includes an operational mode in which ventricular pacing pulses are delivered at a rate that tracks a sinoatrial rate up to an appropriate maximum atrial tracking rate (MATR) value determined by the system. In one example, the MATR value is based on a patient activity level and a hemodynamic maximum rate (HMR) determined from a QRS-to-$S_2$ interval, where $S_2$ is an accelerometer-generated fiducial correlative to aortic valve closure (AVC). In a further example, a correlation between the QRS-to-$S_2$ interval and heart rate is established, and the MATR is based on the patient activity level and heart rate. In a further example, a lower rate threshold for providing antitachyarrhythmia therapy is modified based on the MATR. For example, when the MATR exceeds a default value of the antitachyarrhythmia therapy lower rate threshold, the threshold tracks the MATR. In another example, the MATR value is based on an active time between the QRS complex and a subsequent maximum slope point on a heart impedance signal during the same cardiac cycle.

In one example, the system provides a method including measuring a subinterval of a patient's cardiac cycle correlative to a hemodynamic maximum rate indicator, and establishing a maximum atrial tracking rate based at least in part on the hemodynamic maximum rate indicator.

In another example, the system includes a ventricular sensing channel to detect a QRS complex during a cardiac cycle. An accelerometer is adapted to detect a fiducial of a heart acceleration signal correlative to an aortic valve closure occurring during the cardiac cycle after the QRS complex, and to detect a patient activity level. A controller is adapted for calculating a maximum atrial tracking rate based at least in part on the activity level and a time interval between the QRS complex and the fiducial.

Other aspects of the system will become apparent upon reading the following detailed description of the invention, viewing the drawings that form a part thereof, and viewing the claims that, together with the scope of equivalents to which they are entitled, define the scope of the present invention.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

This document discusses, among other things, a cardiac rhythm management system including an operational mode in which pacing pulses are delivered at a rate that tracks a sinoatrial rate up to an appropriate maximum atrial tracking rate value determined by the system. The present methods and apparatuses will be described in applications involving implantable medical devices including, but not limited to, implantable cardiac rhythm management systems such as pacemakers, cardioverter/defibrillators, pacer/defibrillators, biventricular or other multi-site coordination devices (which coordinate the nature of the heart contraction and may, but need not affect the rate of heart contractions), and drug delivery systems. However, it is understood that the present methods and apparatuses may be employed in unimplanted devices, including, but not limited to, external pacemakers, cardioverter/defibrillators, pacer/defibrillators, biventricular or other multi-site coordination devices, monitors, programmers and recorders, whether such devices are used for providing a diagnostic, a therapy, or both a diagnostic and a therapy.

Figure 1:
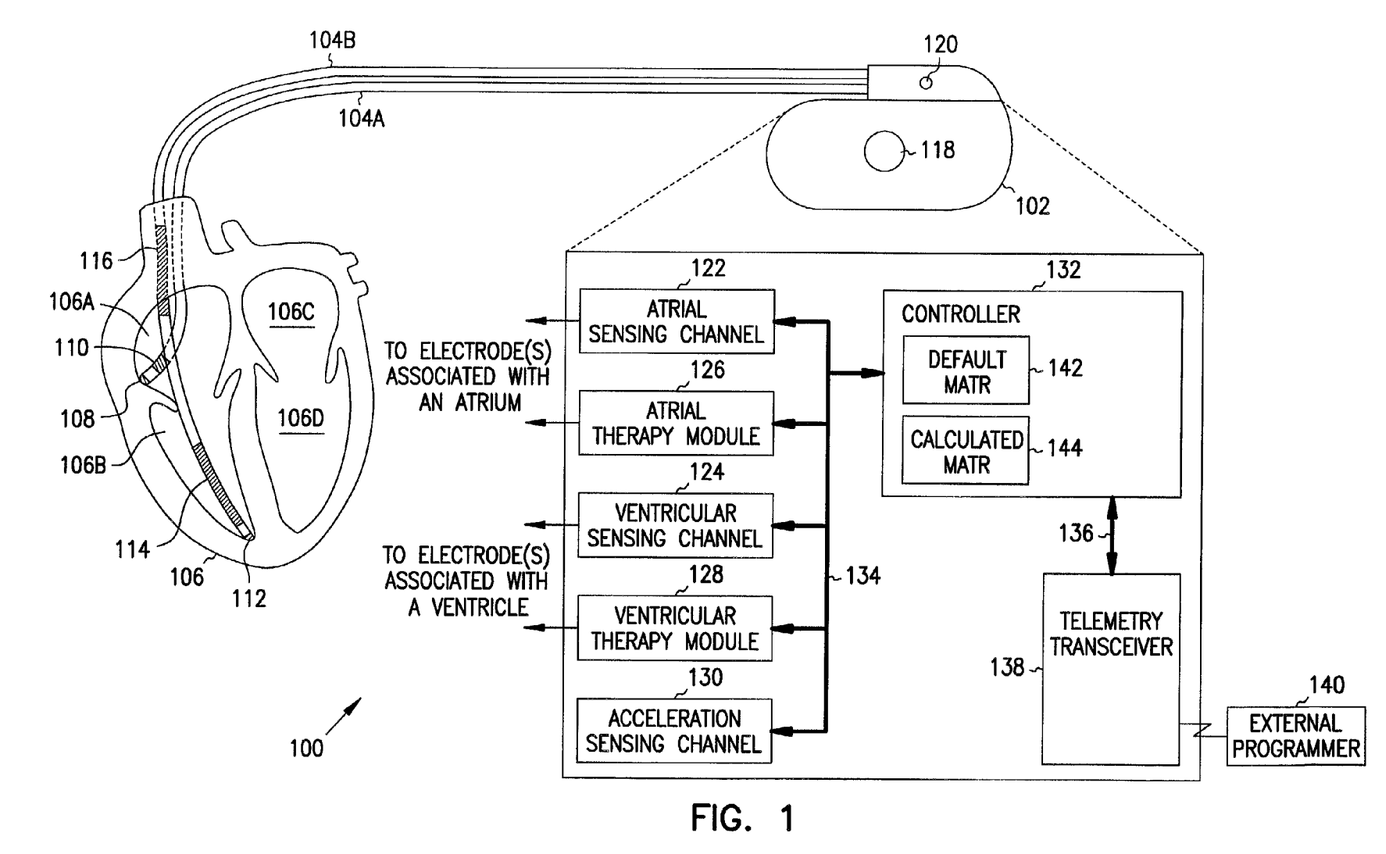
FIG. 1 is a schematic illustration of an example of portions of a cardiac rhythm management system and portions of an environment in which it is used.

FIG. 1 is a schematic illustration of an example of portions of a cardiac rhythm management system 100 and portions of an environment in which it is used. In this example, system 100 includes, among other things, a cardiac rhythm management device 102, which is coupled by one or more leads, such as 104A–B to heart 106. Heart 106 includes at least four chambers: right atrium 106A, right ventricle 106B, left atrium 106C, and left ventricle 106D.

In this example, lead 104A includes an electrode associated with right atrium 106A, such as electrode 108 and/or electrode 110 for sensing atrial heart signals and/or providing atrial pacing pulses. An electrode is "associated" with a particular heart chamber by inserting it into that heart chamber, by inserting it into a portion of the heart's vasculature that is close to that heart chamber, by epicardially placing the electrode outside that heart chamber, or by any other technique of configuring and situating an electrode for sensing signals and/or providing therapy with respect to that heart chamber. Lead 104B includes an electrode, such as electrode 112 or 114, such as for sensing ventricular heart signals and/or providing ventricular pacing pulses. In this example, lead 104B also includes an electrode, such as electrode 116 associated with a right atrium or superior vena cava (SVC), for providing a defibrillation shock in conjunction with electrode 114 or one or more other electrodes.

Device 102 may also include other electrodes, such as housing electrode 118 and/or header electrode 120, which are useful for, among other things, unipolar sensing of heart signals and/or unipolar delivery of contraction-evoking pacing stimulations or defibrillation shocks in conjunction with one or more of the electrodes 108, 110, 112, 114, and 116 associated with heart 106. Alternatively, bipolar sensing and/or pacing and/or defibrillation may be used, such as bipolar atrial sensing and/or pacing between electrodes 108 and 110, or bipolar ventricular sensing and/or pacing between electrodes 112 and 114.

Device 102 includes a sensing module for sensing heart activity signals. The sensing module includes an atrial sensing channel 122 and a ventricular sensing channel 124, each of which is coupled to one or more of the electrodes for sensing electrical depolarizations, corresponding to heart chamber contractions. Such electrical depolarizations of the heart tissue include atrial depolarizations, referred to as P-waves, and ventricular depolarizations, referred to as QRS complexes. A typical QRS complex is a rapid sequence of three signal excursions away from a baseline in sequentially switching polarity, with the first excursion referred to as a Q-wave, the second (typically the largest) excursion referred to as an R-wave, and the third excursion referred to as the S-wave. In one example, detecting a QRS complex includes peak-detecting or level-detecting the R-wave portion of the QRS complex. A ventricular heart signal also includes ventricular repolarizations, referred to as T-waves, which occur after respective QRS complexes in preparation for a subsequent ventricular contraction. This P-Q-R-S-T nomenclature is commonly used to refer to signals obtained from body surface electrocardiograph features; it is understood, however, that in this document, the same nomenclature also pertains to corresponding features of intracardiac electrograms.

In this example, device 102 includes an atrial therapy module 126, coupled to one or more electrodes for delivering an atrial pacing pulse to induce an atrial heart contraction. Moreover, device 102 also includes a ventricular therapy module 128, coupled to one or more ventricular electrodes for delivering a ventricular pacing pulse to induce a ventricular heart contraction and/or a ventricular defibrillation shock to interrupt an episode of ventricular fibrillation detected by ventricular sensing channel 124.

Device 102 also includes an acceleration sensing channel 130. Acceleration sensing channel 130 includes an accelerometer capable of sensing the patient's motion or activity as well as accelerations produced by the heart itself as it contracts and expands to pump blood through the patient's circulatory system. Such heart accelerations include an "$S_2$ heart sound" or other fiducial associated with closure of the heart's aortic valve. One example of a suitable acceleration sensing channel 130 for detecting the $S_2$ heart sound associated with aortic valve closure (AVC) is discussed in Carlson et al. U.S. Pat. No. 5,792,195, entitled "Acceleration Sensed Safe Upper Rate Envelope for Calculating the Hemodynamic Upper Rate Limit For a Rate Adaptive Cardiac Rhythm Management Device," which is assigned to Cardiac Pacemakers, Inc., and incorporated by reference herein in its entirety. Acceleration sensing channel 130 includes bandpass frequency filtering for passing heart sounds, which are in a frequency range that is approximately between 10 Hz and 140 Hz, and patient activity, which is in a frequency range that is approximately between 1 Hz and 10 Hz. Acceleration sensing channel 130 also includes integration or lowpass filtering circuits, such as for integrating a magnitude or squared acceleration signal over a short time period to obtain a smoothed signal representative of the energy of the acceleration signal in the patient activity frequency band.

Device 102 also includes a controller 132 or other microsequencer capable of executing instructions. Controller 132 is coupled by bus 134 to atrial sensing channel 122, ventricular sensing channel 124, atrial therapy module 126, ventricular therapy module 128, and acceleration sensing channel 130. In one embodiment, controller 132 is also coupled by bus 136 to telemetry transceiver 138, which is configured for wireless communication with a remote device, such as external programmer 140.

Among other things, controller 132 executes instructions for issuing triggering and other control signals to ventricular therapy module 128 to issue ventricular pacing pulses to heart 106 for evoking responsive ventricular heart contractions. In one or more modes of operation, referred to as atrial tracking modes, the ventricular pacing pulses are each delivered in response to intrinsic atrial contractions detected by atrial sensing channel 122 after a time delay referred to as an AV delay. Therefore, in an atrial tracking mode, the paced ventricular heart rate tracks the sensed intrinsic atrial heart rate, referred to as the sinoatrial rate, up to, but not beyond, a maximum atrial tracking rate (MATR). Controller 132 further includes an algorithm for calculating a physiologically appropriate value for the MATR, different from a base or default MATR stored in register 142. The calculated MATR is then stored in register 144.

Figure 2:
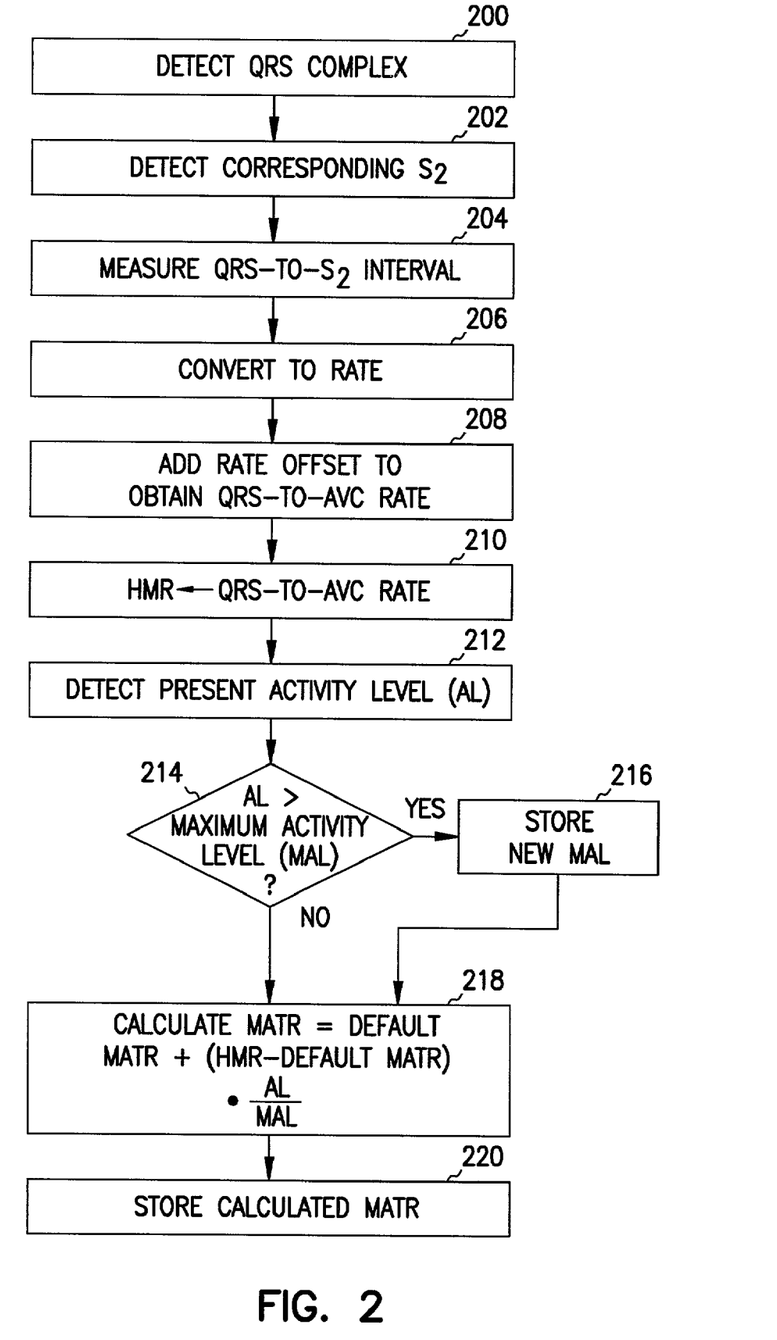
FIG. 2 is a flow chart illustrating an example of how a physiologically appropriate maximum atrial tracking rate (MATR) is calculated.

FIG. 2 is a flow chart illustrating an example of how a physiologically appropriate MATR is calculated by controller 132. At 200, a QRS complex associated with a ventricular heart contraction is detected. In this document, the term "QRS complex" refers to both the depolarization associated with a sensed ventricular heart contraction as well as the depolarization associated with a paced ventricular heart contraction (sometimes referred to as an "evoked response."). Moreover, for a paced ventricular contraction, the "QRS complex" also includes any pacing pulse that triggered the evoked response. At 200, a sensed QRS complex is detected by ventricular sensing channel 124; a paced QRS complex is detected either by sensing the pace or its evoked response using the ventricular sensing channel 124, or by the issuance of a control signal by controller 132 that triggers the pace evoking the resulting ventricular contraction. Subsequently, during the same cardiac cycle, at 202, a S2 heart sound associated with the corresponding aortic valve closure (and deemed an indication or fiducial representative thereof) is sensed by acceleration sensing channel 130. At 204, a time interval between the QRS complex and the S2 heart sound is measured, using a timer in controller 132. This QRS-to-$S_2$ time interval, which is a subinterval of the patient's cardiac cycle, is stored in a register. At 206, the QRS-to-$S_2$ time interval (in milliseconds) is converted into a rate (in beats per minute). The QRS-to-$S_2$ rate is equal to 60,000 divided by the QRS-to-$S_2$ time interval. At 208, a rate offset value is added to the QRS-to-$S_2$ rate to obtain a rate corresponding to the QRS-to-AVC (aortic valve closure) time interval. At 210, this QRS-to-AVC rate is deemed a desired hemodynamic maximum rate (HMR) indicator and stored in a register. At 212, the patient's then existing activity level (AL) is detected using acceleration sensing channel 130. The AL is derived from the energy of the acceleration signal within the patient activity frequency band, as discussed above, with additional smoothing. At 214, if that present AL exceeds a maximum activity level (MAL) over a preceding predetermined longer time interval (e.g., several hours, 24 hours, several days, a week, etc.), then the present AL is stored as the MAL at 216. One example of methods and apparatuses for detecting patient activity over a period of time is discussed in Kadhiresan et al. U.S. Pat. No. 6,135,970, entitled "Method and Apparatus for Assessing Patient Well-Being," which is assigned to Cardiac Pacemakers, Inc., and which is incorporated herein by reference in its entirety. At 218, if the present AL does not exceed the MAL, then a physiologically appropriate MATR is calculated as:

Calculated MATR=Default MATR+(HMR−Default MATR)·(AL/MAL)

The base or default MATR is programmed (e.g., by the factory or by the physician) to a particular value that is approximately between 100 beats per minute and 150 beats per minute, such as about 120 beats per minute. At 220, the calculated MATR is stored in a register.

During subsequent delivery of ventricular pacing pulses in an atrial tracking mode, the paced ventricular heart rate only tracks the sensed intrinsic atrial heart rate up to the calculated MATR. When the detected atrial rate exceeds the MATR, the ventricular pacing pulses are limited in some fashion, such as, for example, by issuing one ventricular pace pulse for every two (or more) sensed atrial heart depolarizations. This effectively maintains the paced ventricular heart rate at a safe value at high sensed atrial rates. Moreover, because the calculated MATR is physiologically based on the HMR obtained from the particular patient, it allows ventricular pacing (and coordination or cardiac resynchronization therapy for patients requiring such therapy) to track the atrial rate up to a higher value, for some patients, than the corresponding default MATR. For active patients, needing higher ventricular pacing rates during exercise, this may be a substantial benefit.

Figure 3:
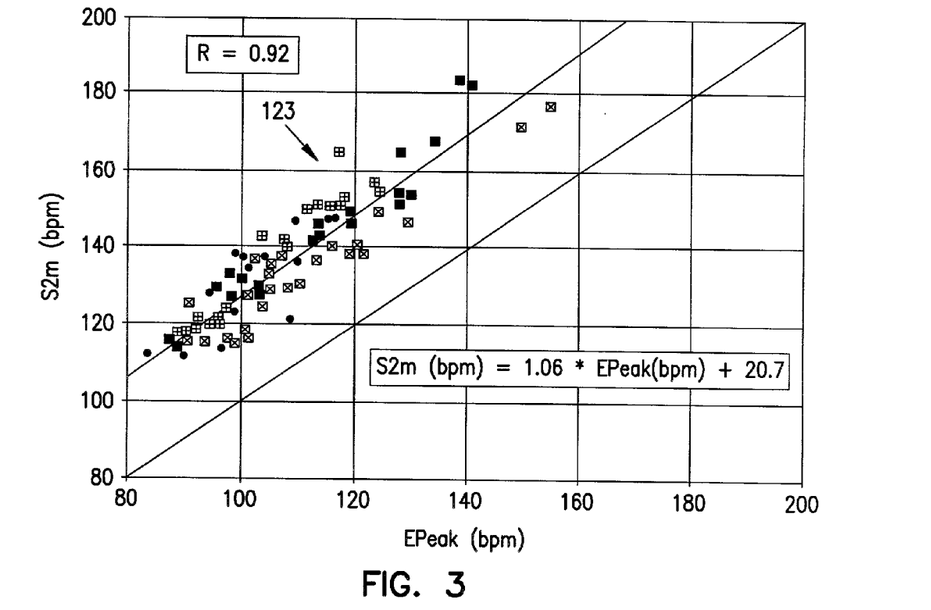
FIG. 3 is a graph of data illustrating S2m (in beats per minute) vs. EPeak (in beats per minute), where S2m=60,000/(QRS-to-$S_2$ interval), in milliseconds, and EPeak=60,000/(QRS-to-AVC interval), in milliseconds.

FIG. 3 is a graph of data 300 illustrating S2m (in beats per minute) vs. EPeak (in beats per minute), where S2m=60,000/(QRS-to-$S_2$ interval), in milliseconds, and EPeak=60,000/(QRS-to-AVC interval), in milliseconds. Data 300 was obtained from a number of patients and at a number of different heart rates. As discussed above, the QRS-to-AVC interval is the time interval between a QRS complex and a subsequent Doppler ultrasound indicated aortic valve closure occurring later during the same cardiac cycle. The QRS-to-$S_2$ interval is the corresponding time interval between that QRS complex and the subsequent accelerometer-indicated $S_2$ heart sound that is also associated with aortic valve closure. Data 300 illustrates a strong correlation (R=0.92) between the rate associated with the accelerometer QRS-to-$S_2$ interval and the rate associated with the Doppler-indicated QRS-to-AVC interval. Data 300 indicates that this relationship can be expressed as S2m (bpm)=1.06·EPeak (bpm)+20.7. Therefore, by subtracting a constant value of 20.7 beats per minute from the rate corresponding to the QRS-to-$S_2$ interval, such as at 208 of FIG. 2, an approximate value of the rate corresponding to the QRS-to-AVC time interval is obtained. Since the slope of the above equation is close to one, no slope correction is required, however, in a further example, such a slope correction is also performed to obtain additional accuracy in translating from the QRS-to-$S_2$ interval rate to the QRS-to-AVC interval rate to obtain a representative HMR for determining the MATR.

In one example, the technique illustrated in FIG. 2 for calculating a physiologically-based MATR is carried out around the time device 102 is implanted in the patient (after acquiring enough patient activity data to establish an MAL). Then, device 102 is placed in an atrial tracking mode that delivers ventricular pacing pulses at a rate that tracks the sensed atrial rate up to the calculated MATR. In another example, the technique illustrated in FIG. 2 is carried out occasionally or periodically (e.g., monthly, weekly, daily, hourly, etc.) to update the calculated MATR even after the time around which device 102 is implanted in the patient. In a further example, the technique illustrated in FIG. 2 is carried out on a beat-by-beat basis to update the physiologically calculated MATR each cardiac cycle. In such an example, averaging, lowpass filtering, or other smoothing could be carried out to limit the degree to which the physiologically calculated MATR fluctuates on a beat-by-beat basis.

In another example, the technique illustrated in FIG. 2 for calculating a physiologically-based MATR is carried out repeatedly in the patient over a range of ventricular heart rates. In one such example, the patient is placed on a treadmill for exercise to raise the heart rate. After such treadmill exercise is stopped, the ventricular heart rate is measured as it slowly returns toward its resting value. At various values of the declining ventricular heart rate, the technique illustrated in 200 through 210 of FIG. 2 is used to calculate the HMR corresponding to that heart rate. These values are used to create a map of HMR vs. heart rate that is stored in memory in controller 132. Then, at a later time, the MATR is calculated (e.g., occasionally, periodically, or even on a beat-by-beat basis) by measuring the then-existing heart rate (e.g., ventricular heart rate), selecting a corresponding MATR from the previously-created HMR vs. heart rate map, and then using the technique in 212 through 220 of FIG. 2 to calculate the MATR.

FIGS. 1–3 illustrate, among other things, particular examples of using a hemodynamic maximum rate indicator to establish a maximum atrial tracking rate such as, for example, by using a time interval between a QRS complex and an aortic valve closure to derive a hemodynamic maximum rate indicator. Alternative techniques exist for deriving a hemodynamic maximum rate indicator. One suitable example of obtaining a hemodynamic maximum rate indicator is based on an "active time" measurement. The "active time" refers to a time between the onset of a heart contraction and the point where a line passing through two points on the fast filling segment of a heart impedance waveform reaches an impedance level corresponding to the end-diastole impedance of the preceding beat. Example methods and apparatuses for performing the "active time" technique are discussed in Spinelli U.S. Pat. No. 5,235,976 entitled "Method and Apparatus for Managing and Monitoring Cardiac Rhythm Using Active Time As the Controlling Parameter," which is assigned to Cardiac Pacemakers, Inc., and which is incorporated herein by reference in its entirety. The "active time" technique provides an alternative hemodynamic maximum rate indicator, which is used to limit the maximum atrial tracking rate.

In a further example, the calculated MATR is used to modify the delivery of antitachyarrhythmia therapy (e.g., antitachyarrhythmic pacing therapy and/or defibrillation shocks) provided by device 102. For example, certain cardiac rhythm management systems provide tiered antitachyarrhythmia therapy, that is, different antitachyarrhythmia therapies are provided based on which one of a plurality of rate zones a sensed ventricular or other heart rate falls in when the tachyarrhythmia episode is occurring. One example of rate-zone-based tiered therapy is discussed in Krig et al. U.S. Pat. No. 6,151,524, entitled "Apparatus and Method for Treating Ventricular Tachyarrhythmias," which is assigned to Cardiac Pacemakers, Inc., and which is incorporated herein by reference in its entirety.

Figure 4:
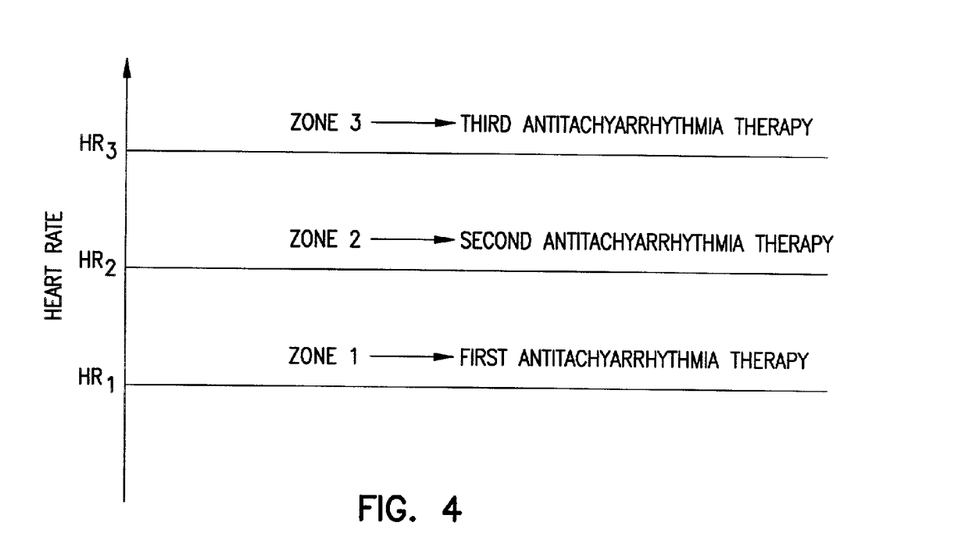
FIG. 4 is a schematic illustration example of three rate zones corresponding to different antitachyarrhythmia therapies provided by a cardiac rhythm management device.

FIG. 4 is a schematic illustration example of three rate zones corresponding to different antitachyarrhythmia therapies provided by cardiac rhythm management device 102. When a tachyarrhythmia is detected, if the heart rate exceeds a first rate threshold, $HR_1$, but does not exceed a second rate threshold $HR_2$, a first antitachyarrhythmia therapy is provided. When the tachyarrhythmia is detected, if the heart rate exceeds the second rate threshold $HR_2$, but does not exceed a third rate threshold, $HR_3$, a second antitachyarrhythmia therapy is provided. When the tachyarrhythmia is detected, if the heart rate exceeds the third rate threshold $HR_3$, a third antitachyarrhythmia therapy is provided. The rate thresholds $HR_1$, $HR_2$, and $HR_3$ are typically programmable by the physician at the time the cardiac rhythm management device is implanted. In one embodiment, if the MATR calculated by device 102 exceeds one or more of the programmed rate thresholds, device 102 increases at least one of the rate thresholds, thereby moving the corresponding zone up to a higher threshold rate value. For example, if the MATR calculated by device 102 exceeds $HR_1$, then device 102 moves $HR_1$ to a value that equals or exceeds the calculated MATR. Similarly, if the subsequently recalculated MATR later falls to a value that is lower than the $HR_1$ value programmed by the physician, then device 102 returns $HR_1$ to its programmed value. In this manner, the calculated MATR is used to adjust a rate zone threshold or other criteria for providing antitachyarrhythmia therapy.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A method including:
   detecting one or more atrial depolarizations;
   measuring a subinterval of a patient's cardiac cycle to obtain a hemodynamic maximum rate indicator;
   establishing a maximum atrial tracking rate based at least in part on the hemodynamic maximum rate indicator; and
   providing ventricular pacing, in response to one or more of the sensed atrial depolarizations, at a ventricular pacing rate that is limited by the maximum atrial tracking rate.

2. The method of claim 1, in which measuring the subinterval includes:
   detecting a portion of a QRS complex;
   detecting an indication of an aortic valve closure; and
   measuring an indication of a time interval between the detected QRS complex and the detected aortic valve closure.

3. The method of claim 2, in which detecting an indication of an aortic valve closure includes detecting an acceleration fiducial correlative to the aortic valve closure.

4. The method of claim 3, in which detecting the acceleration fiducial includes detecting an S2 heart sound.

5. The method of claim 4, in which measuring the indication of the time interval between the detected QRS complex and the detected aortic valve closure includes:
   converting a measured time interval between the detected QRS complex and the S2 heart sound into a heart rate; and
   adding a rate offset thereto to obtain the indication of the time interval between the detected QRS complex and the detected aortic valve closure.

6. The method of claim 1, in which establishing the maximum atrial tracking rate includes:
   providing a base value of the maximum atrial tracking rate;
   detecting a present activity level of the patient;
   detecting a maximum activity level over a period of time; and
   computing the maximum atrial tracking rate by scaling a difference between the hemodynamic maximum rate indicator and the base value of the maximum atrial tracking rate by a ratio of the present activity level to the maximum activity level, and adding the scaled difference to the base value of the maximum atrial tracking rate to establish the maximum atrial tracking rate.

7. The method of claim 1, further including:
   providing a first tachyarrhythmia therapy rate threshold; and
   adjusting the first tachyarrhythmia therapy rate threshold when the maximum atrial tracking rate exceeds the first tachyarrhythmia therapy rate threshold.

8. The method of claim 7, in which adjusting the first tachyarrhythmia therapy rate threshold includes substantially equating the first tachyarrhythmia therapy rate threshold to the maximum atrial tracking rate when the maximum atrial tracking rate exceeds the first tachyarrhythmia therapy rate threshold.

9. The method of claim 1, in which measuring the subinterval of the patient's cardiac cycle correlative to the hemodynamic maximum rate indicator is carried out at a plurality of heart rates to create a correlation between heart rate and the hemodynamic maximum rate indicator.

10. The method of claim 9, in which establishing the maximum atrial tracking rate is based at least in part on the correlation between heart rate and the hemodynamic maximum rate indicator.

11. The method of claim 1, further including adjusting a criteria for providing an antitachyarrhythmia therapy based on the established maximum atrial tracking rate.

12. The method of claim 11, further including increasing a rate threshold for providing an antitachyarrhythmia therapy to a value that is greater than or equal to the established maximum atrial tracking rate.

13. The method of claim 12, further including increasing a lower rate threshold for a lower antitachyarrhythmia therapy zone to a value that is greater than or equal to the established maximum atrial tracking rate.

14. The method of claim 1, in which establishing the maximum atrial tracking rate includes calculating the maximum atrial tracking rate (MATR) as: MATR=Default MATR+(HMR−Default MATR)·(AL/MAL), where Default MATR is a previously programmed value, HMR is a hemodynamic maximum rate based at least in part on the time interval between the QRS complex and the fiducial, AL is the patient activity level, and MAL is a maximum value of the patient activity level over a preceding time period.

15. The method of claim 1, in which measuring the subinterval includes:
   detecting a portion of a QRS complex;
   detecting a heart impedance including variations corresponding to heart contractions;
   detecting a time associated with a maximum slope of the heart impedance; and
   measuring an active time interval between the detected QRS complex and the time associated with the maximum slope of the heart impedance occurring during the same cardiac cycle as the detected QRS complex.

16. The method of claim 15, in which establishing the maximum atrial tracing rate includes using a rate corresponding to the active time interval.

17. A method including:
   measuring a subinterval of a patient's cardiac cycle to obtain a hemodynamic maximum rate indicator;
   establishing a maximum atrial tracking rate based at least in part on the hemodynamic maximum rate indicator;
   providing a first tachyarrhythmia therapy rate threshold; and
   adjusting the first tachyarrhythmia therapy rate threshold when the maximum atrial tracking rate exceeds the first tachyarrhythmia therapy rate threshold.

18. The method of claim 17, in which adjusting the first tachyarrhythmia therapy rate threshold includes substantially equating the first tachyarrhythmia therapy rate threshold to the maximum atrial tracking rate when the maximum atrial tracking rate exceeds the first tachyarrhythmia therapy rate threshold.

19. A method including:
   measuring a subinterval of a patient's cardiac cycle to obtain a hemodynamic maximum rate indicator;
   establishing a maximum atrial tracking rate based at least in part on the hemodynamic maximum rate indicator; and
   increasing a rate threshold for providing an antitachyarrhythmia therapy to a value that is greater than or equal to the established maximum atrial tracking rate.

20. The method of claim 19, further including increasing a lower rate threshold for a lower antitachyarrhythmia therapy zone to a value that is greater than or equal to the established maximum atrial tracking rate.

21. A system including:
   means for measuring a subinterval of a patient's cardiac cycle to obtain a hemodynamic maximum rate indicator;
   means for establishing a maximum atrial tracking rate based at least in part on the hemodynamic maximum rate indicator;
   means for providing a first tachyarrhythmia therapy rate threshold; and
   means for adjusting the first tachyarrhythmia therapy rate threshold when the maximum atrial tracking rate exceeds the first tachyarrhythmia therapy rate threshold.

22. The system of claim 21, in which the means for adjusting the first tachyarrhythmia therapy rate threshold includes means for substantially equating the first tachyarrhythmia therapy rate threshold to the maximum atrial tracking rate when the maximum atrial tracking rate exceeds the first tachyarrhythmia therapy rate threshold.

23. A system including:
   means for measuring a subinterval of a patient's cardiac cycle to obtain a hemodynamic maximum rate indicator;
   means for establishing a maximum atrial tracking rate based at least in part on the hemodynamic maximum rate indicator; and
   means for increasing a rate threshold for providing an antitachyarrhythmia therapy to a value that is greater than or equal to the established maximum atrial tracking rate.

24. The system of claim 23, further including means for increasing a lower rate threshold for a lower antitachyarrhythmia therapy zone to a value that is greater than or equal to the established maximum atrial tracking rate.

25. A method including:
   measuring a subinterval of a patient's cardiac cycle to obtain a hemodynamic maximum rate indicator;
   establishing a maximum atrial tracking rate based at least in part on the hemodynamic maximum rate indicator;
   adjusting a criteria for providing an antitachyarrhythmia therapy based on the established maximum atrial tracking rate; and
   providing an antitachyarrhythmia therapy in response to a detected tachyarrhythmia using the adjusted criteria for providing the antitachyarrhythmia therapy.

26. The method of claim 25, including increasing a rate threshold for providing an antitachyarrhythmia therapy to a value that is greater than or equal to the established maximum atrial tracking rate.

27. A system including:
   means for measuring a subinterval of a patient's cardiac cycle to obtain a hemodynamic maximum rate indicator;
   means for establishing a maximum atrial tracking rate based at least in part on the hemodynamic maximum rate indicator;
   means for adjusting a criteria for providing an antitachyarrhythmia therapy based on the established maximum atrial tracking rate; and
   means for providing an antitachyarrhythmia therapy in response to a detected tachyarrhythmia using the adjusted criteria for providing the antitachyarrhythmia therapy.

28. The system of claim 27, including means for increasing a rate threshold for providing the antitachyarrhythmia therapy to a value that is greater than or equal to the established maximum atrial tracking rate.

29. A system including:
   means for detecting one or more atrial depolarizations;
   means for measuring a subinterval of a patient's cardiac cycle to obtain a hemodynamic maximum rate indicator;
   means for establishing a maximum atrial tracking rate based at least in part on the hemodynamic maximum rate indicator; and
   means for providing ventricular pacing, in response to one or more of the sensed atrial depolarizations, at a ventricular pacing rate that is limited by the maximum atrial tracking rate.

30. The system of claim 29, in which the means for measuring the sub interval includes:
   means for detecting a portion of a QRS complex;
   means for detecting an indication of an aortic valve closure; and
   means for measuring an indication of a time interval between the detected QRS complex and the detected aortic valve closure.

31. The system of claim 30, in which the means for detecting an indication of an aortic valve closure includes means for detecting an acceleration fiducial correlative to the aortic valve closure.

32. The system of claim 31, in which the means for detecting the acceleration fiducial includes means for detecting an S2 heart sound.

33. The system of claim 32, in which the means for measuring the indication of the time interval between the detected QRS complex and the detected aortic valve closure includes:
   means for converting a measured time interval between the detected QRS complex and the S2 heart sound into a heart rate; and
   means for adding a rate offset thereto to obtain the indication of the time interval between the detected QRS complex and the detected aortic valve closure.

34. The system of claim 29, in which the means for establishing the maximum atrial tracking rate includes:
   means for providing a base value of the maximum atrial tracking rate;
   means for detecting a present activity level of the patient;
   means for detecting a maximum activity level over a period of time; and
   means for computing the maximum atrial tracking rate by scaling a difference between the hemodynamic maximum rate indicator and the base value of the maximum atrial tracking rate by a ratio of the present activity level to the maximum activity level, and adding the scaled difference to the base value of the maximum atrial tracking rate to establish the maximum atrial tracking rate.

35. The system of claim 29, further including:
means for providing a first tachyarrhythmia therapy rate threshold; and
means for adjusting the first tachyarrhythmia therapy rate threshold when the maximum atrial tracking rate exceeds the first tachyarrhythmia therapy rate threshold.

36. The system of claim 35, in which the means for adjusting the first tachyarrhythmia therapy rate threshold includes means for substantially equating the first tachyarrhythmia therapy rate threshold to the maximum atrial tracking rate when the maximum atrial tracking rate exceeds the first tachyarrhythmia therapy rate threshold.

37. The system of claim 29, in which the means for measuring the subinterval of the patient's cardiac cycle correlative to the hemodynamic maximum rate indicator includes means for carrying out the measuring at a plurality of heart rates to create a correlation between heart rate and the hemodynamic maximum rate indicator.

38. The system of claim 37, in which means for establishing the maximum atrial tracking rate includes means for establishing the maximum atrial tracking rate based at least in part on the correlation between heart rate and the hemodynamic maximum rate indicator.

39. The system of claim 29, further including means for adjusting a criteria for providing an antitachyarrhythmia therapy based on the established maximum atrial tracking rate.

40. The system of claim 39, further including means for increasing a rate threshold for providing an antitachyarrhythmia therapy to a value that is greater than or equal to the established maximum atrial tracking rate.

41. The system of claim 40, further including means for increasing a lower rate threshold for a lower antitachyarrhythmia therapy zone to a value that is greater than or equal to the established maximum atrial tracking rate.

42. The system of claim 29, in which establishing the maximum atrial tracking rate includes calculating the maximum atrial tracking rate (MATR) as: MATR=Default MATR+(HMR−Default MATR)·(AL/MAL), where Default MATR is a previously programmed value, HMR is a hemodynamic maximum rate based at least in part on the time interval between the QRS complex and the fiducial, AL is the patient activity level, and MAL is a maximum value of the patient activity level over a preceding time period.

* * * * *

UNITED STATES PATENT AND TRADEMARK OFFICE
CERTIFICATE OF CORRECTION

PATENT NO.        : 7,062,323 B2
APPLICATION NO. : 10/040287
DATED             : June 13, 2006
INVENTOR(S)      : Carlson et al.

It is certified that error appears in the above-identified patent and that said Letters Patent is hereby corrected as shown below:

column 10, line 52, in Claim 16, delete "tracing" and insert -- tracking --, therefor.

column 12, line 26, in Claim 29, after "indicator" delete ";".

column 12, line 32, in Claim 30, delete "sub interval" and insert -- subinterval --, therefor.

Signed and Sealed this

Nineteenth Day of September, 2006

JON W. DUDAS
*Director of the United States Patent and Trademark Office*